(12) United States Patent
Yang et al.

(10) Patent No.: US 10,485,773 B2
(45) Date of Patent: *Nov. 26, 2019

(54) BENZENESULFONAMIDE DERIVATIVES AND METHOD FOR TREATING CANCER

(71) Applicant: GONGWIN BIOPHARM HOLDINGS CO., LTD., Grand Cayman (KY)

(72) Inventors: Chuan-Ching Yang, Taipei (TW); Shun-Chi Wu, Taipei (TW); Nanshan Zhong, Taipei (TW); Mao-Yuan Lin, Taipei (TW); Chi-Chiang Tu, Taipei (TW); On Lee, Taipei (TW)

(73) Assignee: GONGWIN BIOPHARM HOLDINGS CO., LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,295

(22) Filed: Jun. 21, 2018

(65) Prior Publication Data

US 2018/0311190 A1    Nov. 1, 2018

Related U.S. Application Data

(63) Continuation-in-part of application No. PCT/US2017/067048, filed on Dec. 18, 2017, which is a continuation of application No. 15/387,221, filed on Dec. 21, 2016, now Pat. No. 9,782,370.

(51) Int. Cl.
| | | |
|---|---|---|
| *A61K 31/18* | (2006.01) | |
| *A61K 47/10* | (2017.01) | |
| *A61K 47/12* | (2006.01) | |
| *A61K 47/20* | (2006.01) | |
| *A61K 9/00* | (2006.01) | |
| *A61P 35/00* | (2006.01) | |
| *A61K 31/337* | (2006.01) | |
| *A61K 31/397* | (2006.01) | |
| *A61K 31/4468* | (2006.01) | |
| *C07D 305/08* | (2006.01) | |

(52) U.S. Cl.
CPC ............ *A61K 31/18* (2013.01); *A61K 9/0019* (2013.01); *A61K 9/0021* (2013.01); *A61K 31/337* (2013.01); *A61K 31/397* (2013.01); *A61K 31/4468* (2013.01); *A61K 47/10* (2013.01); *A61K 47/12* (2013.01); *A61K 47/20* (2013.01); *A61P 35/00* (2018.01); *C07D 305/08* (2013.01)

(58) Field of Classification Search
None
See application file for complete search history.

(56) References Cited

U.S. PATENT DOCUMENTS 9,782,370 B2 * 10/2017 Yang ...................... A61K 31/18

OTHER PUBLICATIONS

Powell et al., Journal of Organic Chemistry (2010), 75(8), pp. 2726-2729.*

\* cited by examiner

*Primary Examiner* — Brian J Davis
(74) *Attorney, Agent, or Firm* — Kramer Amado, P.C.

(57) ABSTRACT

Provided are benzenesulfonamide derivatives or pharmaceutically acceptable salts thereof. Also provided is a method for treating cancer by using a pharmaceutical composition including the benzenesulfonamide derivatives or pharmaceutically acceptable salts thereof and pharmaceutically acceptable carriers.

8 Claims, No Drawings

BENZENESULFONAMIDE DERIVATIVES AND METHOD FOR TREATING CANCER

CROSS-REFERENCE TO RELATED APPLICATIONS

This application is a continuation-in-part of PCT/US2017/067048 filed on Dec. 18, 2017, which is a continuation of Ser. No. 15/387,221, filed on Dec. 21, 2016, now issued as U.S. Pat. No. 9,782,370. The entire disclosures of the prior applications are hereby incorporated by reference herein in their entirety.

BACKGROUND

1. Technical Field

The present disclosure relates to benzenesulfonamide derivatives or pharmaceutically acceptable salts thereof. The present disclosure also relates methods for treating cancer in a subject by administering a pharmaceutical composition containing the benzenesulfonamide derivatives or pharmaceutically acceptable salts thereof.

2. Description of Related Art

Toluene sulfonamide is known as an effective anti-fungal agent and used to treat plant and animal (e.g., human) tissues infected with a fungus. U.S. Pat. Nos. 5,891,454 and 6,727,287 both disclose a toluene sulfonamide-containing composition that exhibits anti-cancer and anti-tumor necrotizing activity.

However, there still remains an unmet need to provide an injectable composition for the more effective and safer treatment of cancer.

SUMMARY

In view of the foregoing, the present disclosure provides a benzenesulfonamide derivative represented by formula (I) or a pharmaceutically acceptable salt thereof:

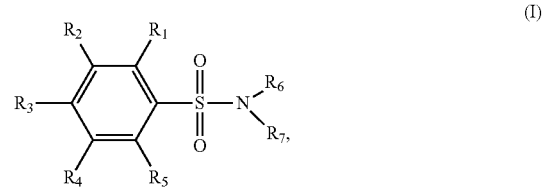

wherein:
$R_1$, $R_2$, $R_4$ and $R_5$ are H;
$R_3$ is a methyl group;
$R_6$ and $R_7$ are independently selected from the group consisting of H, an unsubstituted or substituted $C_3$-$C_6$ cycloalkyl group and an unsubstituted or substituted $C_3$-$C_6$ cycloheteroalkyl group, or $R_6$ and $R_7$ are linked to each other to form an unsubstituted or substituted ring, provided that $R_6$ and $R_7$ are not H at the same time.

The present disclosure also provides a method for treating cancer in a subject in need thereof, comprising administering a therapeutically effective amount of a pharmaceutical composition to the subject, wherein the pharmaceutical composition comprises a benzenesulfonamide derivative represented by formula (I) or a pharmaceutically acceptable salt thereof, and a pharmaceutically acceptable carrier.

DETAILED DESCRIPTION OF THE EMBODIMENTS

The following examples are used to exemplify the present disclosure. A person of ordinary skills in the art can understand the other advantages of the present disclosure, based on the specification of the present disclosure. The present disclosure can also be implemented or applied as described in different specific examples. It is possible to modify or alter the examples for carrying out this disclosure without contravening its spirit and scope for different aspects and applications.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

As used herein, the term "soluble" means that powder of a benzenesulfonamide derivative or a pharmaceutically acceptable salt thereof does not precipitate in solvents such as dimethyl sulfoxide (DMSO) or water but forms a transparent and clear solution or a non-transparent but uniform solution.

The present disclosure provides a benzenesulfonamide derivative represented by formula (I) or a pharmaceutically acceptable salt thereof:

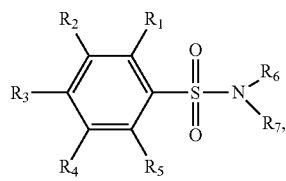

wherein:
$R_1$, $R_2$, $R_4$ and $R_5$ are independently H;
$R_3$ is a methyl group or a carboxyl group;
$R_6$ and $R_7$ are independently selected from the group consisting of H, an unsubstituted or substituted $C_3$-$C_6$ cycloalkyl group and an unsubstituted or substituted $C_3$-$C_6$ cycloheteroalkyl group, or $R_6$ and $R_7$ are linked to each other to form an unsubstituted or substituted ring, provided that $R_6$ and $R_7$ are not H at the same time.

In an embodiment of the present disclosure, the substituted cycloalkyl group, the substituted cycloheteroalkyl group and the substituted ring are independently substituted with a substituent selected from the group consisting of an amide group, a hydroxyl group, a benzyl group and an aminomethyl group. In another embodiment of the present disclosure, the substituent may be further substituted with another substituent.

In an embodiment of the present disclosure, the benezesulfonamide derivative or the pharmaceutically acceptable salt thereof is selected from the group consisting of

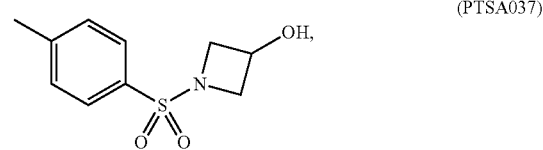

-continued

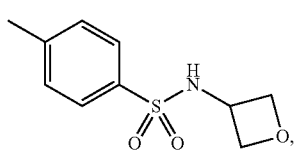
(PTSA040)

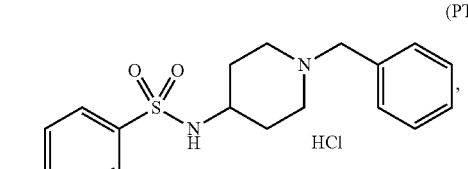
(PTSA052i)

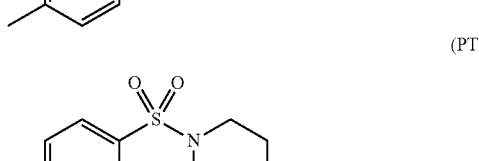
(PTSA055)

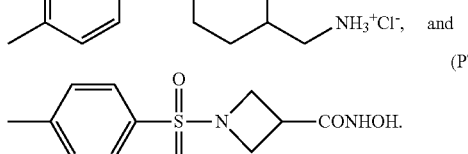
(PTSA067)

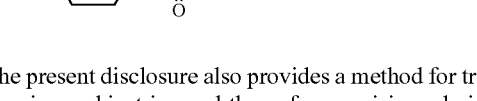

The present disclosure also provides a method for treating cancer in a subject in need thereof, comprising administering a therapeutically effective amount of a pharmaceutical composition to the subject, wherein the pharmaceutical composition comprises a benzenesulfonamide derivative or a pharmaceutically acceptable salt thereof, and a pharmaceutically acceptable carrier.

In an embodiment of the present disclosure, the benzenesulfonamide derivative is represented by formula (I):

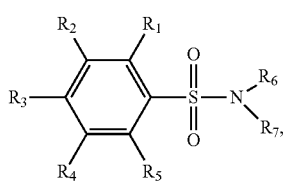
(I)

or a pharmaceutically acceptable salt thereof,
wherein:
$R_1$, $R_2$, $R_4$ and $R_5$ are independently H;
$R_3$ is a methyl group or a carboxyl group;
$R_6$ and $R_7$ are independently selected from the group consisting of H, an unsubstituted or substituted $C_3$-$C_6$ cycloalkyl group and an unsubstituted or substituted $C_3$-$C_6$ cycloheteroalkyl group, or $R_6$ and $R_7$ are linked to each other to form an unsubstituted or substituted ring, provided that $R_6$ and $R_7$ are not H at the same time.

In an embodiment of the present disclosure, the substituted cycloalkyl group, the substituted cycloheteroalkyl group and the substituted ring are independently substituted with a substituent selected from the group consisting of an amide group, a hydroxyl group, a benzyl group and an aminomethyl group.

In an embodiment of the present disclosure, $R_6$ and $R_7$ of the benzenesulfonamide derivative represented by formula (I) are linked to each other to form an unsubstituted or substituted 4- to 6-membered ring, wherein the substituted ring is substituted with a substituent selected from the group consisting of an amide group, a hydroxyl group, a benzyl group and an aminomethyl group. In another embodiment of the present disclosure, $R_6$ and $R_7$ of the benzenesulfonamide derivative represented by formula (I) are independently selected from the group consisting of H, an unsubstituted or substituted $C_3$-$C_6$ cycloalkyl group and an unsubstituted or substituted $C_3$-$C_6$ cycloheteroalkyl group, provided that $R_6$ and $R_7$ are not H at the same time, wherein the substituted cycloalkyl group and the substituted cycloheteroalkyl group are independently substituted with a substituent selected from the group consisting of an amide group, a hydroxyl group, a benzyl group and an aminomethyl group.

In an embodiment of the present disclosure, the benezesulfonamide derivative or the pharmaceutically acceptable salt thereof is selected from the group consisting of

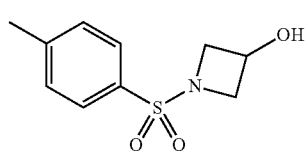
(PTSA037)

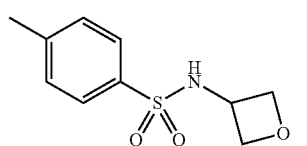
(PTSA040)

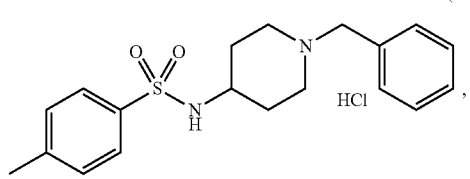
(PTSA052i)

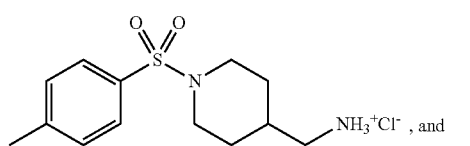
(PTSA055)

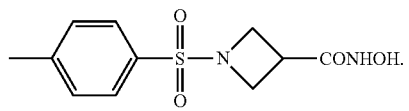
(PTSA067)

In an embodiment of the present disclosure, the pharmaceutically acceptable carrier is selected from the group consisting of a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide (DMSO), alcohol and a combination thereof.

In an embodiment of the present disclosure, the benzenesulfonamide derivative or the pharmaceutically acceptable salt thereof is present in the pharmaceutical composition in an amount of from 0.1% to 50% of the composition by weight. For example, an amount of the benzenesulfonamide derivative or the pharmaceutically acceptable salt thereof in the pharmaceutical composition has a lower limit chosen from 0.1%, 0.2%, 0.5%, 1%, 2.5%, 5%, 10%, 15%, 20%, 25% and 30% of the composition by weight, and an upper limit chosen from 50%, 45%, 40%, 35% and 30% of the composition by weight.

In an embodiment of the present disclosure, the cancer may be at least one selected from the group consisting of liver cancer, lung cancer, breast cancer, head and neck cancer, colon cancer, renal cancer, skin cancer, cervical cancer, prostate cancer, pancreatic cancer and gastric cancer. In another embodiment of the present disclosure, the cancer is liver cancer or lung cancer.

The following are specific embodiments further demonstrating the efficacy of the current disclosure, but not to limit the scope of the current disclosure.

EXAMPLES

Example 1: Preparation of p-TSA Derivatives

Sixty one p-TSA derivatives as shown in Table 1 were chemically synthesized by ligating a functional group to the amino group of p-TSA, while at least one of the —NH groups was remained in the p-TSA derivatives, allowing the solubility of the p-TSA derivatives to be increased. Such derivatives can be divided into 8 major groups based on the characteristics of their functional groups. The first group of the p-TSA derivatives belongs to p-TSA metabolites and the salt thereof. The second group of the p-TSA derivatives belongs to acidic derivatives as being p-TSA prodrugs, wherein a strong electron-withdrawing group was ligated to the amino group of p-TSA, allowing the —NH group of p-TSA to be acidic to form a salt. The third group of the p-TSA derivatives belongs to the amino alcohol group, wherein the p-TSA derivatives with the hydroxyl group were formed by reacting p-toluenesulfonyl chloride with an amino alcohol, and the hydroxyl group of the p-TSA derivatives allows the solubility thereof to be increased. The fourth group of the p-TSA derivatives belongs to the amino ether group, wherein the p-TSA derivatives with the ether group were formed by reacting p-toluenesulfonyl chloride with an amino ether, and the ether group of the p-TSA derivatives allows the solubility thereof to be increased. The fifth group of the p-TSA derivatives belongs to the amino acid group, wherein the p-TSA derivatives with the carboxyl group were formed by reacting p-toluenesulfonyl chloride with an amino acid, and the carboxyl group of the p-TSA derivatives allows the solubility thereof to be increased and the salts thereof to be formed. The sixth group of the p-TSA derivatives belongs to the fluoroamine group, wherein the p-TSA derivatives with the fluoro group were formed by reacting p-toluenesulfonyl chloride with the fluoro group of amines, and the fluoro group of the p-TSA derivatives provides the p-TSA derivatives with specific bioactivity. The seventh group of the p-TSA derivatives belongs to the amino amine group, wherein the p-TSA derivatives with the additional amine group (R—N HCl) were formed by reacting p-toluenesulfonyl chloride with a tertiary amine, and the additional amine group of the p-TSA derivatives allows the solubility thereof to be increased and the salts thereof to be formed. The eighth group of the p-TSA derivatives belongs to the azetidine derivatives of PTSA037 as shown in Table 1, wherein the azetidine derivatives of PTSA037 have better solubility than PTSA037. Each of the p-TSA derivatives has purity greater than 90%.

TABLE 1 p-TSA derivatives

| Groups of p-TSA derivatives | Number | Chemical structure, formula and molecular weight |
|---|---|---|
| p-TSA metabolites and the salts thereof | PTSA001 | 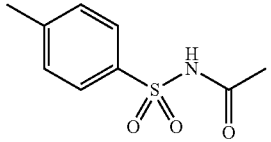<br>Chemical Formula: $C_9H_{11}NO_3S$<br>Molecular Weight: 213.251 |
|  | PTSA002 | 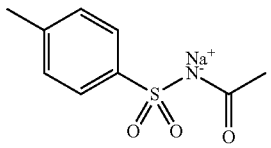<br>Chemical Formula: $C_9H_{10}NO_3S$<br>Molecular Weight: 212.243 |
|  | PTSA004 | 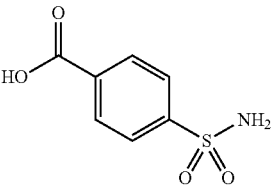<br>Chemical Formula: $C_7H_7NO_4S$<br>Molecular Weight: 201.196 |

TABLE 1-continued p-TSA derivatives

| Groups of p-TSA derivatives | Number | Chemical structure, formula and molecular weight |
|---|---|---|
| | PTSA005 | 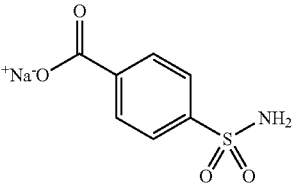<br>Chemical Formula: C$_7$H$_6$NNaO$_4$S<br>Molecular Weight: 223.178 |
| Acidic derivatives | PTSA011 | 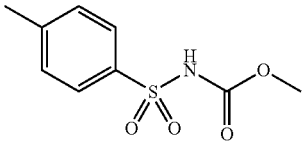<br>Chemical Formula: C$_9$H$_{11}$NO$_4$S<br>Molecular Weight: 229.250 |
| | PTSA012 | 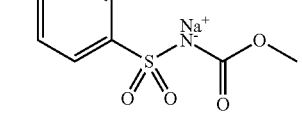<br>Chemical Formula: C$_9$H$_{10}$NNaO$_4$S<br>Molecular Weight: 251.232 |
| | PTSA014 | 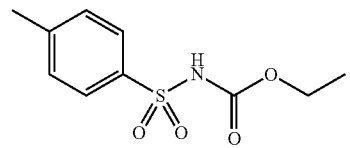<br>Chemical Formula: C$_{10}$H$_{13}$NO$_4$S<br>Molecular Weight: 243.277 |
| | PTSA015 | 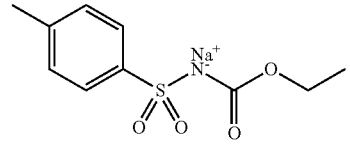<br>Chemical Formula: C$_{10}$H$_{12}$NNaO$_4$S<br>Molecular Weight: 265.259 |
| | PTSA017 | 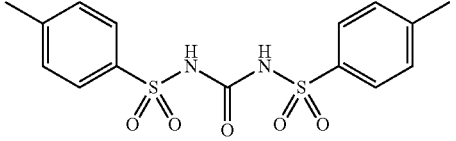<br>Chemical Formula: C$_{15}$H$_{16}$N$_2$O$_5$S$_2$<br>Molecular Weight: 368.422 |

TABLE 1-continued p-TSA derivatives

| Groups of p-TSA derivatives | Number | Chemical structure, formula and molecular weight |
|---|---|---|
| | PTSA018 | 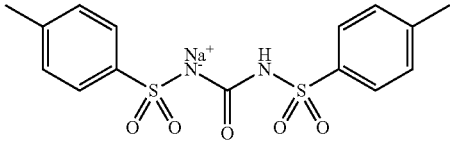<br>Chemical Formula: $C_{15}H_{15}N_2NaO_5S_2$<br>Molecular Weight: 390.404 |
| Amino alcohols | PTSA020 | 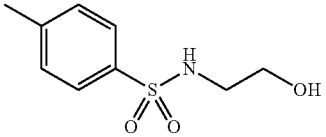<br>Chemical Formula: $C_9H_{13}NO_3S$<br>Molecular Weight: 215.267 |
| | PTSA021 | 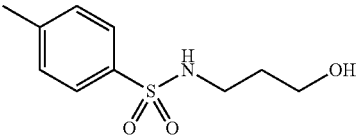<br>Chemical Formula: $C_{10}H_{15}NO_3S$<br>Molecular Weight: 229.294 |
| | PTSA022 | 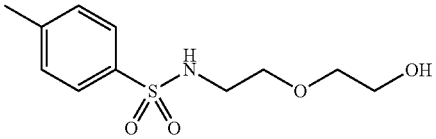<br>Chemical Formula: $C_{11}H_{17}NO_4S$<br>Molecular Weight: 259.320 |
| | PTSA023 | 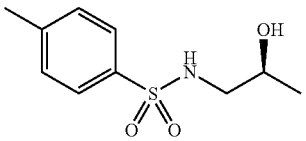<br>Chemical Formula: $C_{10}H_{15}NO_3S$<br>Molecular Weight: 229.294 |
| | PTSA024 | 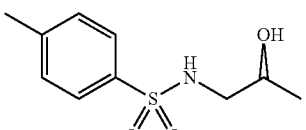<br>Chemical Formula: $C_{10}H_{15}NO_3S$<br>Molecular Weight: 229.294 |
| | PTSA025 | 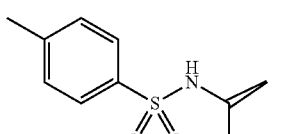<br>Chemical Formula: $C_{10}H_{15}NO_3S$<br>Molecular Weight: 229.294 |

TABLE 1-continued p-TSA derivatives

| Groups of p-TSA derivatives | Number | Chemical structure, formula and molecular weight |
|---|---|---|
| | PTSA026 | 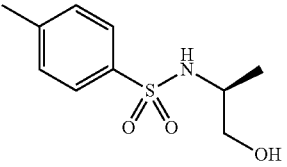<br>Chemical Formula: $C_{10}H_{15}NO_3S$<br>Molecular Weight: 229.294 |
| | PTSA027 | 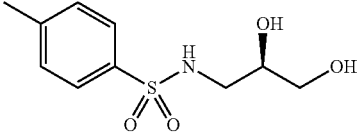<br>Chemical Formula: $C_{10}H_{15}NO_4S$<br>Molecular Weight: 245.293 |
| | PTSA028 | 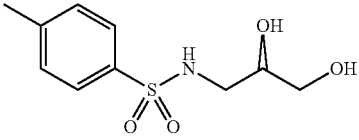<br>Chemical Formula: $C_{10}H_{15}NO_4S$<br>Molecular Weight: 245.293 |
| | PTSA029 | 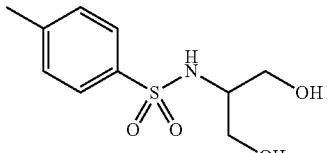<br>Chemical Formula: $C_{10}H_{15}NO_4S$<br>Molecular Weight: 245.293 |
| | PTSA030 | 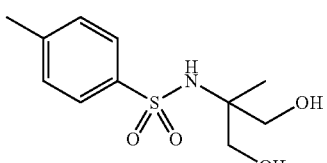<br>Chemical Formula: $C_{11}H_{17}NO_4S$<br>Molecular Weight: 259.320 |
| | PTSA031 | 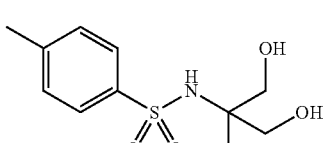<br>Chemical Formula: $C_{11}H_{17}NO_5S$<br>Molecular Weight: 275.319 |

TABLE 1-continued p-TSA derivatives

| Groups of p-TSA derivatives | Number | Chemical structure, formula and molecular weight |
|---|---|---|
| | PTSA032 | 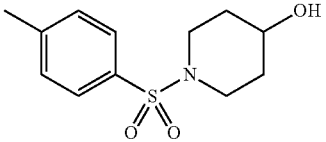<br>Chemical Formula: $C_{12}H_{17}NO_3S$<br>Molecular Weight: 255.332 |
| | PTSA033 | 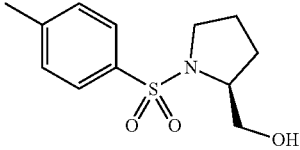<br>Chemical Formula: $C_{12}H_{17}NO_3S$<br>Molecular Weight: 255.332 |
| | PTSA034 | 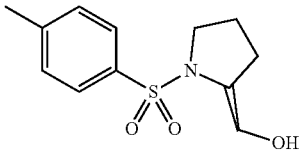<br>Chemical Formula: $C_{12}H_{17}NO_3S$<br>Molecular Weight: 255.332 |
| | PTSA035 | 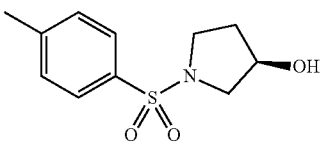<br>Chemical Formula: $C_{11}H_{15}NO_3S$<br>Molecular Weight: 241.305 |
| | PTSA036 | 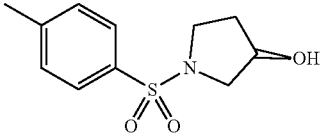<br>Chemical Formula: $C_{11}H_{15}NO_3S$<br>Molecular Weight: 241.305 |
| | PTSA037 | 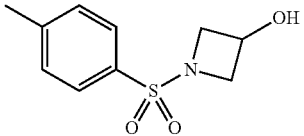<br>Chemical Formula: $C_{10}H_{13}NO_3S$<br>Molecular Weight: 227.278 |
| Amino ethers | PTSA039 | 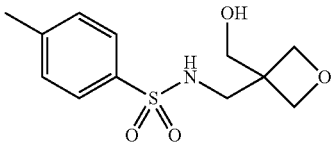<br>Chemical Formula: $C_{12}H_{17}NO_4S$<br>Molecular Weight: 271.331 |

TABLE 1-continued p-TSA derivatives

| Groups of p-TSA derivatives | Number | Chemical structure, formula and molecular weight |
|---|---|---|
| | PTSA040 | 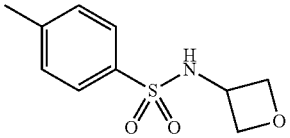<br>Chemical Formula: $C_{10}H_{13}NO_3S$<br>Molecular Weight: 227.278 |
| | PTSA041 | 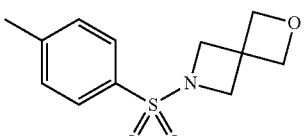<br>Chemical Formula: $C_{12}H_{15}NO_3S$<br>Molecular Weight: 253.316 |
| | PTSA042 | 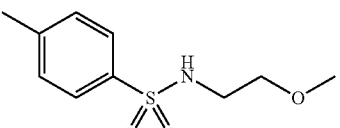<br>Chemical Formula: $C_{10}H_{15}NO_3S$<br>Molecular Weight: 229.294 |
| | PTSA043 | 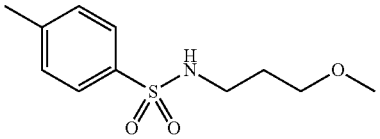<br>Chemical Formula: $C_{11}H_{17}NO_3S$<br>Molecular Weight: 243.321 |
| Amino acids | PTSA044 | 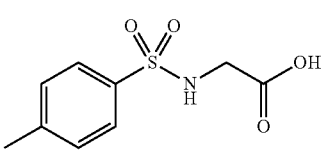<br>Chemical Formula: $C_9H_{11}NO_4S$<br>Molecular Weight: 229.250 |
| | PTSA045 | 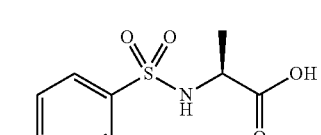<br>Chemical Formula: $C_{10}H_{13}NO_4S$<br>Molecular Weight: 243.277 |
| | PTSA046 | 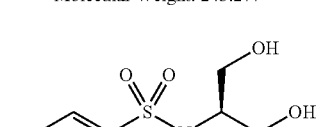<br>Chemical Formula: $C_{10}H_{13}NO_5S$<br>Molecular Weight: 259.276 |

TABLE 1-continued p-TSA derivatives

| Groups of p-TSA derivatives | Number | Chemical structure, formula and molecular weight |
|---|---|---|
| | PTSA047 | 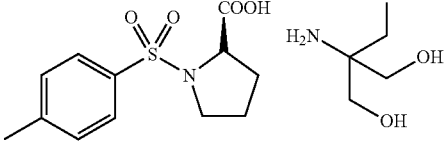<br>Chemical Formula: $C_{16}H_{26}N_2O_7S$<br>Molecular Weight: 390.451 |
| | PTSA048 | 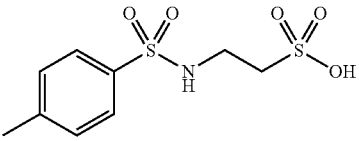<br>Chemical Formula: $C_9H_{13}NO_5S_2$<br>Molecular Weight: 279.325 |
| Fluoroamines | PTSA049 | 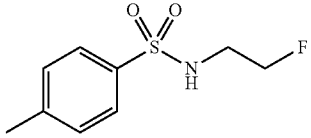<br>Chemical Formula: $C_9H_{12}FNO_2S$<br>Molecular Weight: 217.258 |
| | PTSA050 | 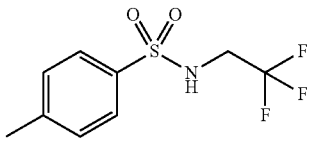<br>Chemical Formula: $C_9H_{10}F_3NO_2S$<br>Molecular Weight: 253.239 |
| Amino amines | PTSA051 | 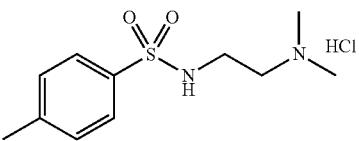<br>Chemical Formula: $C_{11}H_{19}ClN_2O_2S$<br>Molecular Weight: 278.795 |
| | PTSA052 | 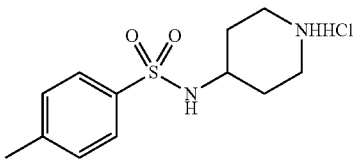<br>Chemical Formula: $C_{12}H_{19}ClN_2O_2S$<br>Molecular Weight: 290.806 |
| | PTSA052i | 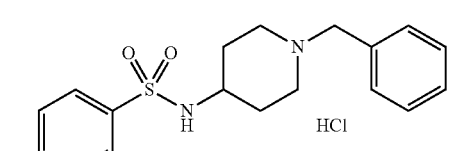<br>Chemical Formula: $C_{19}H_{25}ClN_2O_2S$<br>Molecular Weight: 380.931 |

TABLE 1-continued

| Groups of p-TSA derivatives | Number | Chemical structure, formula and molecular weight |
|---|---|---|
| | PTSA053 | 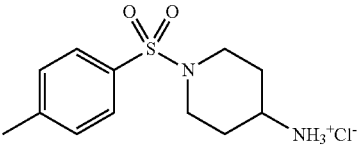<br>Chemical Formula: $C_{12}H_{19}ClN_2O_2S$<br>Molecular Weight: 290.806 |
| | PTSA054 | 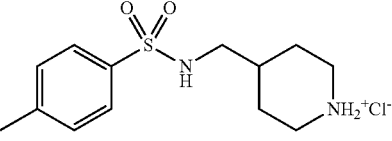<br>Chemical Formula: $C_{13}H_{21}ClN_2O_2S$<br>Molecular Weight: 304.833 |
| | PTSA055 | 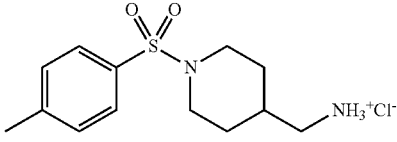<br>Chemical Formula: $C_{13}H_{21}ClN_2O_2S$<br>Molecular Weight: 304.833 |
| | PTSA038 | 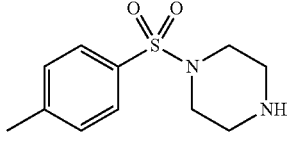<br>Chemical Formula: $C_{11}H_{16}N_2O_2S$<br>Molecular Weight: 240.321 |
| Azetidine derivatives of PTSA037 | PTSA061 | 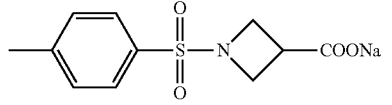<br>Chemical Formula: $C_{11}H_{12}NNaO_4S$<br>Molecular Weight: 277.27 |
| | PTSA062 | 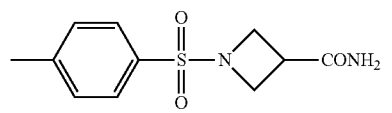<br>Chemical Formula: $C_{11}H_{14}N_2O_3S$<br>Molecular Weight: 254.30 |
| | PTSA063 | 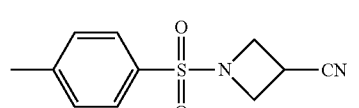<br>Chemical Formula: $C_{11}H_{12}N_2O_2S$<br>Molecular Weight: 236.29 |

TABLE 1-continued

| Groups of p-TSA derivatives | Number | Chemical structure, formula and molecular weight |
|---|---|---|
| | PTSA064 | Chemical Formula: $C_{10}H_{11}F_2NO_2S$<br>Molecular Weight: 247.26 |
| | PTSA065 | Chemical Formula: $C_{10}H_{12}FNO_2S$<br>Molecular Weight: 229.27 |
| | PTSA066 | Chemical Formula: $C_{10}H_{11}NO_3S$<br>Molecular Weight: 225.26 |
| | PTSA067 | Chemical Formula: $C_{11}H_{14}N_2O_4S$<br>Molecular Weight: 270.30 |
| | PTSA068 | Chemical Formula: $C_{11}H_{17}ClN_2O_2S$<br>Molecular Weight: 276.78 |
| | PTSA069 | Chemical Formula: $C_{11}H_{15}NO_3S$<br>Molecular Weight: 241.31 |
| | PTSA070 | Chemical Formula: $C_{10}H_{12}N_2O_3S$<br>Molecular Weight: 240.28 |
| | PTSA071 | Chemical Formula: $C_{11}H_{15}N_3O_3S$<br>Molecular Weight: 269.32 |

TABLE 1-continued p-TSA derivatives

| Groups of p-TSA derivatives | Number | Chemical structure, formula and molecular weight |
|---|---|---|
| | PTSA072 | 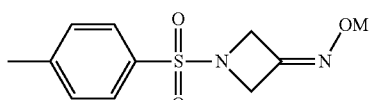<br>Chemical Formula: $C_{11}H_{14}N_2O_3S$<br>Molecular Weight: 254.30 |
| | PTSA073 | 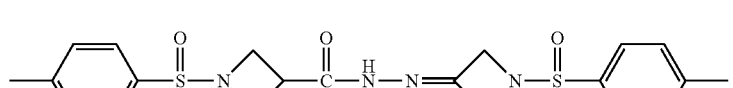<br>Chemical Formula: $C_{21}H_{24}N_4O_5S_2$<br>Molecular Weight: 476.57 |
| | PTSA074 | 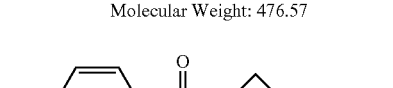<br>Chemical Formula: $C_{10}H_{15}ClN_2O_2S$<br>Molecular Weight: 262.75 |

Example 2: Solubility of the p-TSA Derivatives

Table 2 shows the amounts of each of the p-TSA derivatives for preparing a 3 M solution in DMSO or water. Each of the powder of p-TSA derivatives was duplicated, placed in each 15 mL centrifuge tube, followed by adding 200 μL DMSO or 200 μL water and shaking for 10 to 20 seconds for dissolution observation. If the powder was not dissolved, additional DMSO or water was added, and then the mixture was shaken. The tube was left to stand for 10 minutes for observation if the powder was still not dissolved after adding 1 mL DMSO or 1 mL water. If the powder was still not dissolved after adding 5 mL DMSO or 5 mL water, additional 1 mL DMSO or 1 mL water was added, and then the mixture was shaken for 30 seconds. If the powder was still not dissolved after adding 10 mL DMSO or 10 mL water, the tube was left to stand for 12 to 16 hours and observed on the next day. DMSO or water was added into the tube having the undissolved p-TSA derivatives up to 15 mL, followed by shaking for 30 minutes for observation.

A second dissolution test was performed for the undissolved p-TSA derivatives. Each of 100 mg p-TSA derivatives powder was placed in each of the scintillation vial, followed by adding 500 μL DMSO or 500 μL water and shaking for 30 seconds for dissolution observation. If the powder was not dissolved, additional DMSO or water was added, followed by shaking. The tube was left to stand for 10 minutes if the powder was still not dissolved after adding 1 mL DMSO or 1 mL water.

TABLE 2

Amounts of p-TSA derivatives for solubility test

| p-TSA derivatives | Molecular weight | Amounts for preparing 3M solution in 0.5 mL DMSO or water (g) |
|---|---|---|
| PTSA001 | 213.251 | 0.3198765 |
| PTSA002 | 212.243 | 0.3183645 |
| PTSA004 | 201.196 | 0.301794 |
| PTSA005 | 223.178 | 0.334767 |
| PTSA011 | 229.25 | 0.343875 |
| PTSA012 | 251.232 | 0.376848 |
| PTSA014 | 243.277 | 0.3649155 |
| PTSA015 | 265.259 | 0.3978885 |
| PTSA017 | 368.422 | 0.552633 |
| PTSA018 | 390.404 | 0.585606 |
| PTSA020 | 215.267 | 0.3229005 |
| PTSA021 | 229.294 | 0.343941 |
| PTSA022 | 259.32 | 0.38898 |
| PTSA023 | 229.294 | 0.343941 |
| PTSA024 | 229.294 | 0.343941 |
| PTSA025 | 229.294 | 0.343941 |
| PTSA026 | 229.294 | 0.343941 |
| PTSA027 | 245.293 | 0.3679395 |
| PTSA028 | 245.293 | 0.3679395 |
| PTSA029 | 245.293 | 0.3679395 |
| PTSA030 | 259.32 | 0.38898 |
| PTSA031 | 275.319 | 0.4129785 |
| PTSA032 | 255.332 | 0.382998 |
| PTSA033 | 255.332 | 0.382998 |
| PTSA034 | 255.332 | 0.382998 |
| PTSA035 | 241.305 | 0.3619575 |
| PTSA036 | 241.305 | 0.3619575 |
| PTSA037 | 335.371 | 0.5030565 |
| PTSA038 | 255.332 | 0.382998 |
| PTSA039 | 271.331 | 0.4069965 |
| PTSA040 | 241.305 | 0.3619575 |
| PTSA041 | 253.316 | 0.379974 |
| PTSA042 | 229.294 | 0.343941 |
| PTSA043 | 243.321 | 0.3649815 |
| PTSA044 | 229.25 | 0.343875 |
| PTSA045 | 243.277 | 0.3649155 |
| PTSA046 | 259.276 | 0.388914 |
| PTSA047 | 390.451 | 0.5856765 |
| PTSA048 | 279.325 | 0.4189875 |
| PTSA049 | 217.258 | 0.325887 |

TABLE 2-continued

Amounts of p-TSA derivatives for solubility test

| p-TSA derivatives | Molecular weight | Amounts for preparing 3M solution in 0.5 mL DMSO or water (g) |
|---|---|---|
| PTSA050 | 253.239 | 0.3798585 |
| PTSA051 | 278.795 | 0.4181925 |
| PTSA052 | 290.806 | 0.436209 |
| PTSA052i | 380.93 | 0.571395 |
| PTSA053 | 290.806 | 0.436209 |
| PTSA054 | 304.833 | 0.4572495 |
| PTSA055 | 304.833 | 0.4572495 |
| PTSA061 | 277.27 | 0.415905 |
| PTSA062 | 254.3 | 0.38145 |
| PTSA063 | 236.29 | 0.354435 |
| PTSA064 | 247.26 | 0.37089 |
| PTSA065 | 229.27 | 0.343905 |
| PTSA066 | 225.26 | 0.33789 |
| PTSA067 | 270.3 | 0.40545 |
| PTSA068 | 276.78 | 0.41517 |
| PTSA069 | 241.31 | 0.361965 |
| PTSA070 | 240.28 | 0.36042 |
| PTSA071 | 269.32 | 0.40398 |
| PTSA072 | 254.3 | 0.38145 |
| PTSA073 | 476.57 | 0.714855 |
| PTSA074 | 262.75 | 0.394125 |

Results were shown in Table 3 below, demonstrating that: fifteen p-TSA derivatives were dissolved in both of DMSO and water; forty-four p-TSA derivatives were dissolved only in DMSO; one p-TSA derivative was dissolved only in water; and one p-TSA derivative was undissolved in both of DMSO and water.

TABLE 3

Dissolution of p-TSA derivatives

| | Dissolved in both DMSO and water | Dissolved only in DMSO | Dissolved only in water | Undissolved in both DMSO and water |
|---|---|---|---|---|
| p-TSA metabolites and the salts thereof | PTSA002* | PTSA001 and PTSA004 | PTSA005 | |
| Acidic derivatives (p-TSA prodrugs) | PTSA012, PTSA015, and PTSA018 | PTSA011, PTSA014, and PTSA017 | | |
| Amino alcohol (R-OH) | PTSA020 and PTSA031 | PTSA021, PTSA022, PTSA023, PTSA024, PTSA025, PTSA026, PTSA027, PTSA028, PTSA029, PTSA030, PTSA033, PTSA034, PTSA035, PTSA036, and PTSA037 | | PTSA032 |
| Amino ether (R-O) | | PTSA039, PTSA040, PTSA041, PTSA042, and PTSA043 | | |
| Amino acids (R-COOH) | PTSA047 and PTSA048 | PTSA044, PTSA045, and PTSA046 | | |
| Fluoroamines (R-F) | | PTSA049*, and PTSA050 | | |
| Amino amines (R-N HCl) | PTSA051, PTSA052, PTSA053, and PTSA055 | PTSA052i, PTSA054, and PTSA038 | | |
| PTSA037 derivatives | PTSA061, PTSA068, and PTSA074 | PTSA062, PTSA063, PTSA064, PTSA065, PTSA066, PTSA067, PTSA069, PTSA070, PTSA071, PTSA072, and PTSA073* | | |

*PTSA002, PTSA049 and PTSA073 were not dissolved in DMSO or water in the first dissolution test, but dissolved in DMSO, water or both in the second dissolution test.

As mentioned above, among the sixty-one p-TSA derivatives, except PTSA032 that was not dissolved in neither DMSO nor water, sixty p-TSA derivatives were found soluble in DMSO, whereas only sixteen p-TSA derivatives (including PTSA005) were soluble in water. It could be seen that only about 27% of the tested p-TSA derivatives was soluble in water.

Further, as shown in Tables 4 to 6 below, by comparison with the solubility of p-TSA, it was found that the hydrophilic functional groups ligated to the p-TSA derivatives did not necessarily enhance the solubility thereof.

TABLE 4

Solubility of p-TSA derivatives

| p-TSA derivatives | Amounts for preparing a 3M solution in 0.5 mL DMSO or water (g) | Total volume of DMSO for dissolving the p-TSA derivatives (μL) | Total volume of water for dissolving the p-TSA derivatives (μL) |
|---|---|---|---|
| PTSA001 | 0.3198765 | 510 | insoluble in 15000 |
| PTSA002 | 0.3183645 | insoluble in 15000 | insoluble in 15000 |
| PTSA004 | 0.301794 | 960 (with pipetting) | insoluble in 15000 |
| PTSA005 | 0.334767 | insoluble in 15000 | 10000 |
| PTSA011 | 0.343875 | 560 | insoluble in 15000 |
| PTSA012 | 0.376848 | 680 | 500 |
| PTSA014 | 0.3649155 | 610 | insoluble in 15000 |
| PTSA015 | 0.3978885 | 815 | 500 |
| PTSA017 | 0.552633 | 2000 | insoluble in 15000 |
| PTSA018 | 0.585606 | 2000 | 2500 |
| PTSA020 | 0.3229005 | 490 | 10000 |
| PTSA021 | 0.343941 | 495 | insoluble in 15000 |
| PTSA022 | 0.38898 | 505 | insoluble in 15000 |
| PTSA023 | 0.343941 | 500 | insoluble in 15000 |
| PTSA024 | 0.343941 | 515 | insoluble in 15000 |
| PTSA025 | 0.343941 | 560 | insoluble in 15000 |
| PTSA026 | 0.343941 | 500 | insoluble in 15000 |
| PTSA027 | 0.3679395 | 575 | insoluble in 15000 |
| PTSA028 | 0.3679395 | 620 | insoluble in 15000 |
| PTSA029 | 0.3679395 | 500 | insoluble in 15000 |
| PTSA030 | 0.38898 | 695 | insoluble in 15000 |
| PTSA031 | 0.4129785 | 700 | 10000 |
| PTSA032 | 0.382998 | insoluble in 15000 | insoluble in 15000 |
| PTSA033 | 0.382998 | 500 | insoluble in 15000 |
| PTSA034 | 0.382998 | 505 | insoluble in 15000 |
| PTSA035 | 0.3619575 | 490 | insoluble in 15000 |
| PTSA036 | 0.3619575 | 530 | insoluble in 15000 |
| PTSA037 | 0.5030565 | 605 | insoluble in 15000 |
| PTSA038 | 0.382998 | 680 | insoluble in 15000 |
| PTSA039 | 0.4069965 | 500 | insoluble in 15000 |
| PTSA040 | 0.3619575 | 475 | insoluble in 15000 |
| PTSA041 | 0.379974 | 4000 | insoluble in 15000 |
| PTSA042 | 0.343941 | 475 | insoluble in 15000 |
| PTSA043 | 0.3649815 | 505 | insoluble in 15000 |
| PTSA044 | 0.343875 | 600 | insoluble in 15000 |
| PTSA045 | 0.3649155 | 2000 | insoluble in 15000 |
| PTSA046 | 0.388914 | 845 | insoluble in 15000 |
| PTSA047 | 0.5856765 | 2000 | 2500 |
| PTSA048 | 0.4189875 | 2000 | 10000 |
| PTSA049 | 0.325887 | insoluble in 15000 | insoluble in 15000 |
| PTSA050 | 0.3798585 | 590 | insoluble in 15000 |
| PTSA051 | 0.4181925 | 1500 | 1000 |
| PTSA052 | 0.436209 | 2000 | 5000 |
| PTSA052i | 0.571395 | 4000 | insoluble in 15000 |
| PTSA053 | 0.436209 | 15000 | 2500 |
| PTSA054 | 0.4572495 | 740 | insoluble in 15000 |
| PTSA055 | 0.4572495 | 2000 | 3000 |
| PTSA061 | 0.415905 | 2500 | 750 |
| PTSA062 | 0.38145 | 3000 | insoluble in 15000 |
| PTSA063 | 0.354435 | 900 | insoluble in 15000 |
| PTSA064 | 0.37089 | 750 | insoluble in 15000 |
| PTSA065 | 0.343905 | 2500 | insoluble in 15000 |
| PTSA066 | 0.33789 | 3000 | insoluble in 15000 |
| PTSA067 | 0.40545 | 870 | insoluble in 15000 |
| PTSA068 | 0.41517 | 4000 | 4500 |
| PTSA069 | 0.361965 | 880 | insoluble in 15000 |
| PTSA070 | 0.36042 | 850 | insoluble in 15000 |

TABLE 4-continued

Solubility of p-TSA derivatives

| p-TSA derivatives | Amounts for preparing a 3M solution in 0.5 mL DMSO or water (g) | Total volume of DMSO for dissolving the p-TSA derivatives (μL) | Total volume of water for dissolving the p-TSA derivatives (μL) |
|---|---|---|---|
| PTSA071 | 0.40398 | 1500 | insoluble in 15000 |
| PTSA072 | 0.38145 | 4500 | insoluble in 15000 |
| PTSA073 | 0.714855 | insoluble in 15000 | insoluble in 15000 |
| PTSA074 | 0.394125 | 2500 | 10000 |

TABLE 5

Comparison of solubility of p-TSA and p-TSA derivatives in DMSO and water

| p-TSA and p-TSA derivatives | Solubility in DMSO (mg/mL) | Solubility in water (mg/mL) |
|---|---|---|
| PTSA | 785.95 | <50 |
| PTSA037 | 831.50 | <50 |
| PTSA040 | 762.02 | <50 |
| PTSA052i | 142.85 | <50 |
| PTSA055 | 228.62 | 152.42 |
| PTSA067 | 466.03 | <50 |

As shown in Table 6 below, the powder of PTSA002, PTSA049 and PTSA073 were not dissolved in DMSO or water in the first dissolution test, but dissolved in both of DMSO or water in the second dissolution test by use of less (100 mg) powder for dissolving in a larger volume (500 μL) of DMSO or water. Further, the powder of PTSA0032 was still not dissolved in 20 mL DMSO or 20 mL water, and was considered as being undissolved in the desired concentration.

TABLE 6

Solubility of p-TSA derivatives in the second dissolution test

| p-TSA derivatives for the second dissolution test | Amount (g) | Total volume of DMSO for dissolving the p-TSA derivatives (mL) | Total volume of water for dissolving the p-TSA derivatives (mL) |
|---|---|---|---|
| PTSA002 | 0.1 | 8 | 5.25 |
| PTSA032 | 0.1 | insoluble in 20 ml | insoluble in 20 mL |
| PTSA049 | 0.1 | 9.5 | insoluble in 20 mL |
| PTSA073 | 0.1 | 4.04 | insoluble in 20 mL |

Example 3: Effect of the p-TSA Derivatives on Killing Liver and Lung Cancer Cells Human non-small-cell lung cancer cell lines H460 in an amount of $5 \times 10^3$ cells/well or human liver cancer cell lines Hep3B in an amount of $4 \times 10^3$ cells/well was respectively seeded in each well of a 96-well plate and incubated under the condition of 5% $CO_2$ at 37° C. for 24 hours. Further, 25 μL trichloroacetic acid (TCA) was added into each well for fixing cells. After letting to stand for 10 minutes at room temperature, the supernatant of each well was removed, and each well was washed with 200 μL $H_2O$ once.

Each of the sixty p-TSA derivatives was added into each well in an indicated concentration, and incubated for 48 hours. If the p-TSA derivative was seriously precipitated in a tube during dilution, the tube would be left to stand for 5 to 10 minutes, and the supernatant of the tube would be used in this test. The control in this test was performed in the same procedure as described above, except for addition of the p-TSA derivatives.

Each of the plates was then placed in the laminar flow cabinet for 1 hour for air dry. 50 µL 0.4% sulforhodamine B (SRB) dye was added into each well of the 96-well plate. After letting to stand at room temperature for 10 minutes, SRB dye was removed, and each well was washed with 200 µL acetic acid at least one to three times until no dye residue was visually observed.

Each of the plates was then placed in the laminar flow cabinet for 40 minutes to 1 hour for air dry. 1×Tris-Base solution with pH 7.0 to 7.4 was added to each well of the 96-well plate to dissolve the protein complex formed in the bottom of each well, followed by tapping the 96-well plate, allowing the complex in each well to be dissolved uniformly. Absorption of each well under 515 nm was read. The half maximal inhibitory concentration ($IC_{50}$) of each p-TSA derivative against human non-small-cell lung cancer cell lines H460 and human liver cancer cell lines Hep3B was calculated by the formula of:

$$1-([(Tx-Tz)/(Control-Tz)]\times 100\%),$$

wherein Tz indicates the cell population at the time of each p-TSA derivative addition, and Tx indicates the cells treated with tested samples. Each of the experimental group was performed in triplet.

Results were shown in Table 7 below. For the effect on inhibiting human non-small-cell lung cancer cell lines H460, p-TSA dissolved in DMSO was used as a control, and has an $IC_{50}$ value being 3.7191±0.146 mM.

Results showed that PTSA037, PTSA040, PTSA052i, PTSA055 and PTSA067 surprisingly provided lower $IC_{50}$ values than p-TSA about 6 to 20 folds, indicating better capacity for inhibiting the growth of lung cancer cells. Specifically, the $IC_{50}$ values of PTSA037 dissolved in DMSO were 0.2877 mM and 0.2587 mM in the duplicated experiments; the $IC_{50}$ values of PTSA040 dissolved in DMSO were 0.4311 mM and 0.4062 mM in the duplicated experiments; the $IC_{50}$ value of PTSA052i dissolved in DMSO was 0.1414 mM; the $IC_{50}$ value of PTSA055 dissolved in DMSO was 0.6174 mM; the $IC_{50}$ value of PTSA055 dissolved in water was 0.6514 mM; and the $IC_{50}$ value of PTSA067 dissolved in DMSO was 0.2733 mM. p-TSA derivatives other than PTSA037, PTSA040, PTSA052i, PTSA055 and PTSA067 either had higher $IC_{50}$ values than that of p-TSA or provided lower $IC_{50}$ values than that of p-TSA only 2 to 4 folds are not proceeded with further evaluation in this disclosure.

For the effect on inhibiting human liver cancer cell lines Hep3B, p-TSA dissolved in DMSO was used as a control group, and the $IC_{50}$ value thereof was 3.7276±0.274 mM.

Results showed that PTSA037, PTSA040, PTSA052i, PTSA055 and PTSA067 unexpectedly provided lower $IC_{50}$ values than p-TSA about 6 to 20 folds, indicating better capacity for inhibiting the growth of liver cancer cells. Specifically, the $IC_{50}$ values of PTSA037 dissolved in DMSO were 0.2647 mM and 0.2739 mM in the duplicated experiments; the $IC_{50}$ values of PTSA040 dissolved in DMSO were 0.3287 mM and 0.4131 mM in the duplicated experiments; the $IC_{50}$ value of PTSA052i dissolved in DMSO was 0.1369 mM; the $IC_{50}$ value of PTSA055 dissolved in DMSO was 0.596 mM; the $IC_{50}$ value of PTSA055 dissolved in water was 0.6102 mM; and the $IC_{50}$ value of PTSA067 dissolved in DMSO was 0.2607 mM.

From the above, it could be seen that PTSA037, PTSA040, PTSA052i, PTSA055 and PTSA067 provided better effects on inhibiting the growth of human non-small-cell lung cancer cell lines H460 and human liver cancer cell lines Hep3B than that of p-TSA, and could be used as candidates for second-generation drug development.

TABLE 7

$IC_{50}$ values of p-TSA and the derivatives thereof

| p-TSA derivatives | $IC_{50}$ of H460 in water | $IC_{50}$ of H460 in DMSO | $IC_{50}$ of Hep3B in water | $IC_{50}$ of Hep3B in DMSO |
|---|---|---|---|---|
| p-TSA | untested | 3.7191 ± 0.146 mM | untested | 3.7276 ± 0.274 mM |
| PTSA001 | insoluble and not able to be tested | 7.7222 mM | insoluble and not able to be tested | >9 mM |
| PTSA002 | >6.03 mM | >0.27 mM | >6.03 mM | >0.27 mM |
| PTSA004 | insoluble and not able to be tested | 9.6724 mM | insoluble and not able to be tested | >7 mM |
| PTSA005 | >2 mM | insoluble and not able to be tested | >2 mM | insoluble and not able to be tested |
| PTSA011 | insoluble and not able to be tested | 5.4937 mM | insoluble and not able to be tested | 4.561 mM |
| PTSA012 | >5 mM | 6.1144 mM | untested | 7.5 mM |
| PTSA014 | insoluble and not able to be tested | 5.8175 mM | insoluble and not able to be tested | 4.5943 mM |
| PTSA015 | 4.9592 mM | 4.7855 mM | untested | 5.7678 mM |
| PTSA017 | insoluble and not able to be tested | >3 mM | insoluble and not able to be tested | >3 mM |
| PTSA018 | >3 mM | >3 mM | >3 mM | >3 mM |
| PTSA020 | >1 mM | 2.6103 mM | >1 mM | 2.645 mM |
| PTSA021 | insoluble and not able to be tested | 2.4481 mM | insoluble and not able to be tested | 2.8143 mM |
| PTSA022 | insoluble and not able to be tested | 3.6535 mM | insoluble and not able to be tested | 4.7235 mM |
| PTSA023 | insoluble and not able to be tested | 2.8949 mM | insoluble and not able to be tested | 2.6543 mM |
| PTSA024 | insoluble and not able to be tested | 3.2201 mM | insoluble and not able to be tested | 3.8283 mM |
| PTSA025 | insoluble and not able to be tested | 3.1453 mM | insoluble and not able to be tested | 3.543 mM |

TABLE 7-continued

IC$_{50}$ values of p-TSA and the derivatives thereof

| p-TSA derivatives | IC$_{50}$ of H460 in water | IC$_{50}$ of H460 in DMSO | IC$_{50}$ of Hep3B in water | IC$_{50}$ of Hep3B in DMSO |
|---|---|---|---|---|
| PTSA026 | insoluble and not able to be tested | 3.251 mM | insoluble and not able to be tested | 3.9204 mM |
| PTSA027 | insoluble and not able to be tested | 5.3454 mM | insoluble and not able to be tested | 4.1022 mM |
| PTSA028 | insoluble and not able to be tested | 5.529 mM | insoluble and not able to be tested | 5.3593 mM |
| PTSA029 | insoluble and not able to be tested | 1.9651 mM | insoluble and not able to be tested | 3.0544 mM |
| PTSA030 | insoluble and not able to be tested | 3.3027 mM | insoluble and not able to be tested | 4.3146 mM |
| PTSA031 | >1 mM | 3.3068 mM | >1 mM | 4.2096 mM |
| PTSA032 | insoluble and not able to be tested | insoluble and not able to be tested | insoluble and not able to be tested | insoluble and not able to be tested |
| PTSA033 | insoluble and not able to be tested | 1.4237 mM | insoluble and not able to be tested | 1.7556 mM |
| PTSA034 | insoluble and not able to be tested | 1.497 mM | insoluble and not able to be tested | 1.7844 mM |
| PTSA035 | insoluble and not able to be tested | 2.8288 mM | insoluble and not able to be tested | 2.282 mM |
| PTSA036 | insoluble and not able to be tested | 2.5426 mM | insoluble and not able to be tested | 3.403 mM |
| PTSA037 | insoluble and not able to be tested | 0.2877 mM; 0.2587 mM | insoluble and not able to be tested | 0.2642 mM; 0.2739 mM |
| PTSA038 | insoluble and not able to be tested | 1.6177 mM | insoluble and not able to be tested | 1.5695 mM |
| PTSA039 | insoluble and not able to be tested | 4.1571 mM | insoluble and not able to be tested | 3.7395 mM |
| PTSA040 | insoluble and not able to be tested | 0.4311 mM; 0.4062 mM | insoluble and not able to be tested | 0.3287 mM; 0.4131 mM |
| PTSA041 | insoluble and not able to be tested | >2 mM | insoluble and not able to be tested | >2 mM |
| PTSA042 | insoluble and not able to be tested | 2.4911 mM | insoluble and not able to be tested | 2.748 mM |
| PTSA043 | insoluble and not able to be tested | 1.6106 mM | insoluble and not able to be tested | 1.8441 mM |
| PTSA044 | insoluble and not able to be tested | 7.9259 mM | insoluble and not able to be tested | 9.1108 mM |
| PTSA045 | insoluble and not able to be tested | >3 mM | insoluble and not able to be tested | >3 mM |
| PTSA046 | insoluble and not able to be tested | >10 mM | insoluble and not able to be tested | >10 mM |
| PTSA047 | >3 mM | >3 mM | >3 mM | >3 mM |
| PTSA048 | >3 mM | >3 mM | >3 mM | >3 mM |
| PTSA049 | insoluble and not able to be tested | >0.174 mM | insoluble and not able to be tested | >0.174 mM |
| PTSA050 | insoluble and not able to be tested | precipitated and not able to be tested | insoluble and not able to be tested | precipitated and not able to be tested |
| PTSA051 | 1.747 mM | 1.8183 mM | 1.4394 mM | 1.4138 mM |
| PTSA052 | 1.088 mM | 0.9065 mM | 0.9544 mM | 0.919 mM |
| PTSA052i | insoluble and not able to be tested | 0.1414 mM | insoluble and not able to be tested | 0.1369 mM |
| PTSA053 | 0.6909 mM | untested | 0.7696 mM | untested |
| PTSA054 | insoluble and not able to be tested | 1.1654 mM | insoluble and not able to be tested | 0.9352 mM |
| PTSA055 | 0.6514 mM | 0.6174 mM | 0.6102 mM | 0.596 mM |
| PTSA061 | >8.8 mM | >2.25 mM | >8.8 mM | >2.25 mM |
| PTSA062 | untested | >2.25 mM | untested | >2.25 mM |
| PTSA063 | precipitated and not able to be tested | 1.2695 mM | precipitated and not able to be tested | 1.296 mM |
| PTSA064 | emulsified and not able to be tested | >0.713 mM | emulsified and not able to be tested | >0.713 mM |
| PTSA065 | precipitated and not able to be tested | 1.3322 mM | precipitated and not able to be tested | 1.4471 mM |
| PTSA066 | precipitated and not able to be tested | 0.906 mM | precipitated and not able to be tested | 0.733 mM |
| PTSA067 | untested | 0.2733 mM | untested | 0.2607 mM |
| PTSA068 | 1.3892 mM | 1.2692 mM | 1.2984 mM | 1.2545 mM |
| PTSA069 | untested | 2.5785 mM | untested | 3.6231 mM |

TABLE 7-continued

IC$_{50}$ values of p-TSA and the derivatives thereof

| p-TSA derivatives | IC$_{50}$ of H460 in water | IC$_{50}$ of H460 in DMSO | IC$_{50}$ of Hep3B in water | IC$_{50}$ of Hep3B in DMSO |
|---|---|---|---|---|
| PTSA070 | precipitated and not able to be tested | precipitated and not able to be tested | precipitated and not able to be tested | precipitated and not able to be tested |
| PTSA071 | untested | 1.0397 mM | untested | 1.0239 mM |
| PTSA072 | untested | >1.125 mM | untested | >1.125 mM |
| PTSA073 | insoluble and not able to be tested | obviously misty and not able to be tested | insoluble and not able to be tested | obviously misty and not able to be tested |
| PTSA074 | 2.2152 mM | >1.8 mM | 2.1258 mM | >1.8 mM |

The disclosure has been described using exemplary embodiments. However, it is to be understood that the scope of the disclosure is not limited to the disclosed embodiments. On the contrary, it is intended to cover various modifications and similar rearrangements. The scope of the claims therefore should be accorded the broadest interpretation so as to encompass all such modifications and similar arrangements.

What is claimed is:

1. A benzenesulfonamide derivative represented by formula (I) or a pharmaceutically acceptable salt thereof:

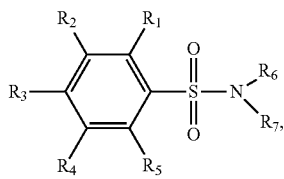

wherein:
$R_1$, $R_2$, $R_4$ and $R_5$ are H;
$R_3$ is a methyl group; and
$R_6$ and $R_7$ are independently selected from the group consisting of H and an unsubstituted or substituted $C_3$-$C_6$ cycloheteroalkyl group, provided that $R_6$ and $R_7$ are not H at the same time, and
wherein the benzenesulfonamide derivative is

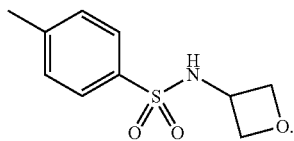

2. A method for treating cancer in a subject in need thereof, comprising administering a therapeutically effective amount of a pharmaceutical composition to the subject, wherein the pharmaceutical composition comprises the benzenesulfonamide derivative or the pharmaceutically acceptable salt thereof of claim 1, and a pharmaceutically acceptable carrier.

3. The method of claim 2, wherein the pharmaceutically acceptable carrier is selected from the group consisting of a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide (DMSO), alcohol and a combination thereof.

4. The method of claim 2, wherein the benzenesulfonamide derivative or the pharmaceutically acceptable salt thereof is present in the pharmaceutical composition in an amount of from 0.10% to 50% by weight.

5. The method of claim 2, wherein the benzenesulfonamide derivative or the pharmaceutically acceptable salt thereof is present in the pharmaceutical composition in an amount of from 1% to 40% by weight.

6. The method of claim 2, wherein the pharmaceutical composition is administered to the subject intratumorally, intravenously, subcutaneously, intradermally, intrathecally, intraperitoneally, intramuscularly, or intrapleuraly.

7. The method of claim 2, wherein the cancer is at least one selected from the group consisting of liver cancer, lung cancer, breast cancer, head and neck cancer, colon cancer, renal cancer, skin cancer, cervical cancer, prostate cancer, pancreatic cancer and gastric cancer.

8. The method of claim 7, wherein the cancer is liver cancer or lung cancer.

* * * * *

UNITED STATES PATENT AND TRADEMARK OFFICE
CERTIFICATE OF CORRECTION

PATENT NO. : 10,485,773 B2  
APPLICATION NO. : 16/014295  
DATED : November 26, 2019  
INVENTOR(S) : Chuan-Ching Yang et al.

Page 1 of 1

It is certified that error appears in the above-identified patent and that said Letters Patent is hereby corrected as shown below:

On the Title Page

Please DELETE:
"Inventors:
Chuan-Ching Yang (Taipei, TW); Shun-Chi Wu (Taipei, TW); Nanshan Zhong (Taipei, TW); Mao-Yuan Lin (Taipei, TW); Chi-Chiang Tu (Taipei, TW); On Lee (Taipei, TW)"

And insert therefor:
--Inventors:
Chuan-Ching Yang (Taipei, TW); Shun-Chi Wu (Taipei, TW); Nanshan Zhong (Guangzhou City, CN); Mao-Yuan Lin (Taipei, TW); Chi-Chiang Tu (Taipei, TW); On Lee (Taipei, TW)--

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*